United States Patent [19]

Hubner

[11] Patent Number: 4,562,723
[45] Date of Patent: Jan. 7, 1986

[54] METHOD OF AND APPARATUS FOR THE MEASUREMENT OF SUBTERRANEAN ATMOSPHERIC PARAMETERS

[76] Inventor: Hans J. Hubner, Katthagen 24, 4400 Münster, Fed. Rep. of Germany

[21] Appl. No.: 635,324

[22] Filed: Jul. 27, 1984

[51] Int. Cl.⁴ .......................................... G01N 27/12
[52] U.S. Cl. ...................................... 73/23; 73/1 G; 340/633; 422/94
[58] Field of Search ............ 73/23, 1 G; 340/632, 340/633, 634; 364/571, 582, 580, 497, 498; 422/94, 98

[56] References Cited

U.S. PATENT DOCUMENTS

| | | | |
|---|---|---|---|
| 3,427,862 | 2/1969 | Hubner | 73/23 |
| 3,845,288 | 10/1974 | Cornyn, Jr. et al. | 364/582 |
| 4,231,249 | 11/1980 | Zuckerman | 73/23 |
| 4,369,647 | 1/1983 | Shigemori et al. | 340/634 |
| 4,464,653 | 8/1984 | Winner | 73/23 |
| 4,475,378 | 10/1984 | Boutonnat et al. | 340/634 |
| 4,485,666 | 12/1984 | Higgins et al. | 73/23 |

FOREIGN PATENT DOCUMENTS

| | | |
|---|---|---|
| 3027051 | 2/1982 | Fed. Rep. of Germany. |
| 3138046 | 4/1982 | Fed. Rep. of Germany. |
| 3243542 | 5/1984 | Fed. Rep. of Germany. |
| 1564981 | 4/1980 | United Kingdom. |

OTHER PUBLICATIONS

"Ein frei programmierbares mikroprozessorgesteuertes Datensystem . . . " by D. Voigt, published in messen+prüfen/automatik—Jul./Aug. 1982.
"Grundlösungen von Aufgaben zur Weiterverarbeitung . . . " by G. Strohrmann, Marl published in Regelungstechnische Praxis 24, Jahrgang 1982 HEFT 8.
"Die Zuverlässigkeit von Messsystemen" by Dr. P. Profos published in Handbuch der Industriellen Messtechnik (Vulkan-Verlag Dr. W. Classen Nachf. GmbH & Co. KG. Essen, 1978).
"Sicher vor allen Gasgefahren durch VABOTEC-TOR-EX" Gas Messung (Gesellschaft für GerätebaumbH & Co. KG) (6/1982 3000 B+M).

Primary Examiner—Stephen A. Kreitman

[57] ABSTRACT

A measuring and evaluating device and method for mine galleries and the like can monitor the various parameters of the atmosphere and normalize the parameters for display and storage in the device. In an emergency the danger-posing operations of the device are shut down although the memory is maintained and, for further safety, a detector which may pose a danger may be inactivated and replaced by a less precise detector for the same parameter but which poses no danger.

50 Claims, 9 Drawing Figures

METHOD OF AND APPARATUS FOR THE MEASUREMENT OF SUBTERRANEAN ATMOSPHERIC PARAMETERS

CROSS REFERENCE TO RELATED APPLICATIONS

The present application is related to my copending application Ser. No. 493,696, filed May 11, 1983 now U.S. Pat. No. 4,526,028 entitled: PROCESS AND DEVICE FOR INDICATING AND EVALUATING ENVIRONMENTAL PARAMETERS and based upon a German application No. P 32 17 798.4, filed May 12, 1982. This application is also related to concurrently filed copending applications; Ser. No. 635,323 and Ser. No. 635,329. Reference may also be had to German patent document (Open Application DE-OS No. 32 43 542) which, although published prior to the filing of this application, is not a reference and which, like the other applications mentioned previously, is hereby incorporated by reference in its entirety herein.

FIELD OF THE INVENTION

My present invention relates to a method of measuring and evaluating parameters of an enrivonmental atmosphere, especially a subterranean atmosphere and particularly for the monitoring of mine environment conditions, i.e. various parameters of the ventilating atmosphere of mine tunnels, galleries and shafts. The invention thus also relates to a method of measuring such parameters and to the use of at least one measuring device for at least one of these parameters which can provide a measurement of the magnitude of the parameter and which can report, i.e. display, and thereafter store the magnitude, e.g. as a function of time.

BACKGROUND OF THE INVENTION

The measurement and evaluating of environmental parameters and especially the measurement of a characteristic of a surrounding atmosphere, is necessary for a variety of applications, e.g. for long-term information gathering with respect to the environment and for short-term information collection for immediate evaluation and interpretation. This is especially the case where the measurement may contain noxious, a toxic or explosive gases, such measurement being necessary in many cases for the survival and safety of personnel exposed to the atmosphere. The results of such measurements can be used to initiate or control ventilation or some other action, e.g. evacuation or rescue.

It is known to utilize at least one measuring device to measure at least one such parameter, e.g. methane concentration, for example, in subterranean sites, i.e. mine tunnels, galleries and shafts, and to store the measured values or magnitudes of the parameter in a written form with the values being introduced into a book or the like. In mining applications it is known to provide a so-called weather book in which one enters as a function of location and time the various values determined by the measurement of the aforementioned parameters so that even after a long period of time it is possible to review the measurement. The evaluating or analysis of the measured values is effected at a later time, for example using comparison tables.

In many cases it has been found that the measured and evaluated magnitudes of the environment which are obtained in the afore-described manner do not constitute or contain optimum information since the boundary conditions under which the measurements are obtained are either inexact or are insufficiently known to enable the information to be utilized. In certain cases, moreover, certain measurements are not meaningful because of the lack of other measurements. For example, physiology plays a role in the sense that the air temperature also may not be meaningful because it may be measured at a high relative humidity or a low relative humidity so that the temperature measurements are meaningful only if relative humidity is also given.

Similarly, a given gas concentration of toxic, noxious or explosive gases may be more or less dangerous depending upon other parameters of the atmosphere and other conditions.

As a practical matter, earlier methods of monitoring the various parameters of a mine or like atmosphere have proven to be unsatisfactory in that they have not supplied sufficiently clear, complete and utilizable data to satisfy the requirements for efficient mine operation and personnel safety.

OBJECTS OF THE INVENTION

It is the principal object of the present invention to provide an improved method of monitoring at least one environmental parameter and evaluating the same whereby the disadvantages of earlier systems are obviated.

Another object of this invention is to provide an improved method of operating a measuring system of the aforedescribed type which can yield especially clear and complete data, which is rapid in function and which is reliable. Still another object of this invention is to improve upon the measurement and evaluating the environmental atmospheric parameters of a mine gallery, tunnel and shaft which can increase the reliability of such measurements and facilitate the manipulation of data obtained.

It is also an object of this invention to provide an improved apparatus for carrying out the method of this invention, i.e. an improved apparatus for measuring and monitoring at least one parameter of an environmental atmosphere.

SUMMARY OF THE INVENTION

These objects and others are attained, in accordance with the present invention, in a method of measuring an environmental parameter under the conditions described, wherein, after measuring the magnitude of the parameter in the measuring device, in response to an automatic or manual triggering of the measurement reading, this measured parameter or at least one of the measured parameters is normalized or standardized and the standardized or normalized parameter is reported and/or stored alone or together with the absolute measured value.

The term "normalized" is here used in its relatively broad sense to refer to a calibration of the absolute magnitude obtained by measurement so that the result represents the measured parameter as determined by a standard and selected form. The standard values are based upon the absolute magnitude, as well as a linearization of a measurement curve.

Normalization implies that there is a certain relationship between the absolute magnitude and an outputted variable and that based upon some other factor, either predetermined data or relationship, the absolute magnitude is converted into the variable.

The specific normalization or standardization intended by the present invention will depend, of course, on the parameter which is measured and of course the parameter with respect to which the normalization or standardization is to be effective.

For example, it is possible to normalize the measured air temperature to the air pressure at the earth's surface and to a certain predetermined air velocity so that a more meaningful relative working temperature can be generated as the normalized measured value whose effect upon the physical safety of personnel exposed to the temperature can be determined directly. In other cases the normalization may only represent a zero correction, a correction in the sensitivity of a measuring system or the like, e.g. in cases in which drift may occur.

Utilizing the method of the present invention, influences upon a measured parameter can be built into the outputted parameter value.

The method of the invention can be effected in various ways in which only certain examples are described below:

For example, if one works with a measured parameter whose magnitude is not only a function of various other parameters of the ambient atmosphere but also depends upon the response curve of the respective measuring device, it is not possible to carry out the normalization simply by introducing a constant factor in the normalization. Indeed, it is imperative that the normalization be effected in the form of a function, e.g. of the parameter measured and/or of the other parameters or by providing a function which may have been predetermined and which gives a correct value of the magnitude in dependance upon the absolute value or measured value of the parameter. In both cases, the normalization is effected utilizing a predetermined normalization function and can use a function control circuit between the output of the measuring device and the recording or reporting circuit, i.e. a display or other registration circuit which has a transfer function identical to the correction function.

However, it is not always possible to generate a normalization function in advance or to calculate such a function. More commonly the normalization function must be empirically determined. In this case I provide for the calculation or generation of the normalization function by a series of standard measurements of a parameter. Only then are the absolute measurements taken and recalculated in accordance with the thus generated normalization function so that the normalized measured values can be displayed (reported) and/or stored.

If a zero correction is required, this method provides at least one standard measurement at the zero parameter to effect zero correction.

For the calculation or generation of complicated normalization function, especially utilizing a measuring device which suffers changes in the absolute value of the measured magnitude of the parameter with changing sensitivity of the device, I provide that the standard measurement should be effected with at least one intermediate value calibrating measurement.

If, in addition to the zero correction measurement and intermediate value calibration measurement is effected, a straight line normalization function can be calculated whose zero represents an intersection with one of the axes. From the comparison of the intermediate value calibration measurement with the zero correction measurement, the slope of this line can be determined.

The aforementioned standardization measurements can be effected in an atmosphere in which the relevant parameter is exactly 0. The measurement results under these conditions in this atmosphere can be stored at the zero correction and can be later used for calculation of the measuring function. A further standardization measurement at a different new value, preferably close to the expected measured value is used as the intermediate value calibration measurement and provides a further correction value which can be stored and utilized to generate or calculate the normalization function. Based upon both of these measured values, I can calculate a linear normalization function which generally proves to be highly accurate. It will be understood that the normalization function or curve thus generated is precise at least at two measurement points used as a basis therefore, is particularly valuable because it can accurately reset the zero, and is fairly precise in between these points and beyond the intermediate value calibration point although nonlinearities and discontinuities and the like may nevertheless introduce similar errors. Since a purely calculatable correction is effected in accordance with the invention, systematic measuring-technological and like errors in the measurement of the parameters can be overcome without the complicated functions hitherto required which generally implied iterative setting, correction of the zero shift, correction of the sensitivity, after-correction of the zero, after-correction of the sensitivity . . . in preparing the measurement.

The measurement of the parameter required for the normalization can be effected simultaneously with the measurement of the parameter whose value is to be normalized or the measurements can be effected in time-spaced relationship.

It has been indicated earlier that each parameter requires a different normalization. Many parameters need no normalization since the direct measurements of these parameters are effective for the evaluation without such normalization. In each case, the measurement of each parameter can be normalized in a parameter-specific manner.

It has also been found to be advantageous to linearize the measured value by the respective parameters.

For storage of the measured values of the respective parameters, I prefer to use a time-dependent storage which also allows the time to be recovered at which the associated magnitude of a particular parameter is achieved. Such a time-dependent storage can be indirect, e.g. by providing the successive items of information in a certain succession or a recording medium. In addition or alternatively, the information may be recorded as site-dependent data. For example, each parameter measurement may be associated with a site for location code number. The location from which the measurement is taken can also be calculated from a time-dependent measurement.

The storage of these normalized and, if desired, absolute measured values of the different parameters can basically, as previously, be recorded in writing in a weather book for subterranean application. With modern electronic means, however, it is also possible and indeed preferred to provide an appropriate memory in the measuring device, i.e. to integrate the memory in the measuring device. In this case the stored measured values of the parameters can be transferred continuously or from time to time to a central computer and evaluated, storage display at or under the control of this computer.

When the normalization function is relatively complicated, it can be based upon an empirically generated mathematical normalization curve.

In the latter case I have found it to be advantageous to specify the generation of the normalization function by approximating it with a polygonal trace which is used for the measuring function. Only at the beginning in the calculation or empirical derivation of the normalization function is considerable storage space required. Thereafter only the polygonal trace itself need be stored as the normalization function. A polygonal trace is a trace made up of straight line section and greatly simplifies the generation and the electronic storage of the trace. It is possible, therefore, to utilize practically the entire storage capacity for correlating the data which will form the polygonal trace and then to utilize only a small fraction of the storage space to record the normalization function in the form of approximating polygonal trace, thereby leaving the balance of the storage space available for the registering of measured values. In one embodiment of this aspect of the invention, the maximum expected range of the measured values of the parameter is divided into a given number of polygonal trace sections, especially $2^n$ polygonal sections, preferably 16 such sections ($n=4$). The independent variable in the use of the method of the invention preferably is the measured value so that this range is broken into the given number of sections. The use of a power of 2 to determine the number of such sections simplifies the storage in conventional binary data storage systems.

Usually the widths of all of the polygonal sections are equal. This has been found to be advantageous for most normalization functions. However, for extremely steep or sharply changing normalization functions, the widths of the polygonal sections can be selected to be different.

According to another feature of the invention, measuring errors which develop during measurement of the parameter are compensated. If, during the measuring process, the measurement of the parameter yields a measuring error which is greater than the calculation error resulting from calculation of the normalization function, the number and/or width of the polygonal sections can be selected on the basis of the magnitude of the measuring error. The number and/or width of the polygonal sections for all normalization functions can be the same and once a determination of the measuring error is made, can be fixed based upon this error. It is, however, also possible when the number and/or width of the polygonal sections differs from the magnitude defined by the measuring error to take this into consideration. Naturally it is completely senseless to seek a highly exact proximation of a normalization function by the polygonal trace when the measuring error is greater than the calculation error, i.e. greater than the maximum deviations of the polygon trace from the normalization function. In other words, according to the invention, the approximation of the normalization function by the polygon trace is made so that the calculation error is greater or equal to the expected measurement error.

The polygonal trace which had been used as the starting point for the normalization function can be generated by calculation from standard measurements of the parameter or empirically as previously noted, the standard measurements can be carried out in an atmosphere in which the relevant parameter is exactly 0 so that the resulting zero measurement can be used for zero. correction as well as for calculation of the zero for the standardization function. Further measurements can be carried out at intermediate values of the parameter to establish intermediate calibration values as described and, of course, the normalization trace made up of the polygonal segments can be utilized in the manner described.

According to another aspect of the invention, the method is used to improve the reliability of the measurement even in the case of a failure of a measuring device or in the case in which a measuring device must be taken out of service.

According to this aspect of the invention, from time to time the measured value of the parameter whose measurements are subjected to failure, are monitored, the interval between such monitoring being selected so that safety is not a factor and a dangerous condition cannot arise. Alternatively or in addition, the measurement and storage is effected in the measuring device even during the failure so that the measured results can be monitored.

Either or both of these alternatives prevent the development of a failure condition from detrimentally affecting the monitoring of the parameter in the mine shaft or tunnel.

In the first case it is possible to carry out the periodic monitoring of the measurement at such relatively brief intervals by comparison to the time it takes for a failure condition to develop that immediately upon the development of such a condition the failure is detected.

In the second case, where a failure is to be cleared, it is only the remote transmission of data which may be interrupted and this in part may be remedied by intermediate storage of the data in one or more of the measuring devices. According to another feature of the invention, the measuring unit can include a measuring device of especially high precision which can be utilized for measuring a parameter, e.g. a methane concentration with a limited range, for example below the lower explosive limit, while the unit can also include a second device, possibly of less explosive construction and passage which can be utlized for measuring higher concentrations of methane. In the event of failure of the first device and/or the attainment of safety limits for the operation of the first device, the second device can be utilized.

The first device can, for example, use the catalytic combustion method of determing the concentration of methane while the second device can use a thermal conductivity method.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
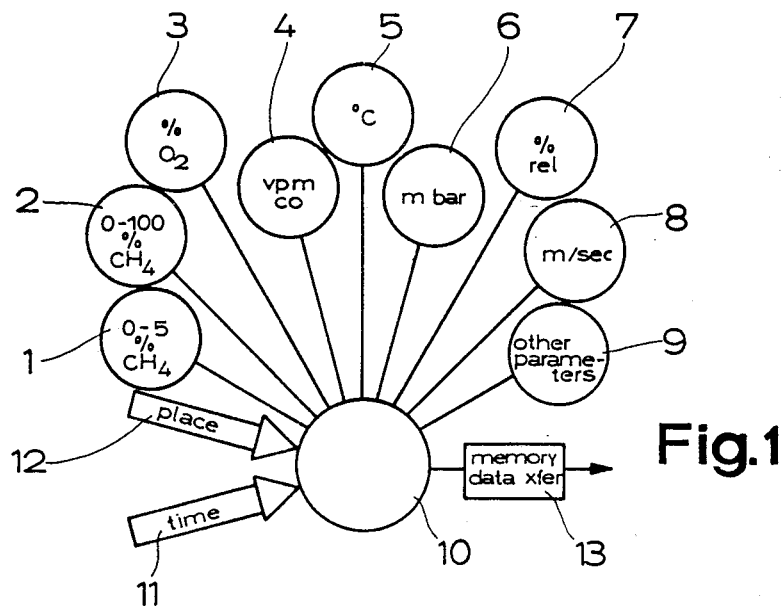
FIG. 1 is a schematic diagram of the functioning of the system embodying the invention for measuring and evaluating of environmental parameters at a subterranean site, i.e. in a mine gallery or tunnel.

In FIG. 1, as described in my copending application Ser. No. 493,696 to which reference may be had at this point, I show a device 10 which is used for measuring, indicating and evaluating a variety of environmental parameters and especially the parameters of a mine atmosphere.

These parameters include various gas concentrations 1-4, air temperature 5, air pressure 6, relative humidity 7, air velocity 8 and not specifically defined additional parameters which are generally represented at 9. All of these parameters and the respective magnitudes are obtained by respective sensors of the device 10 which also receives inputs 11 and 12 representing the time and the place at which the measurements are taken.

Input 1 may represent methane concentrations between 0 and 5% and may utilize a high precision catalytic combustion measuring device which, at levels above the explosive limit can be cut-off and replaced by the measuring device 2 which can be utilized for methane concentrations of 0 to 100% and employs the thermal conductivity measurement systems.

The oxygen-measuring system is represented at 3 and can utilize an electronic process as defined in application Ser. No. 635,329 and as described in this latter application, the measurement of the oxygen concentration can be utilized with suitable calculation as a substitute for either or both of the methane concentration measurements for safety.

The carbon monoxide concentration measurement represented at 4 can result from the use of a chemisorption technique with a metallic oxide semi-conductor. All of these measuring systems are described in the latter copending application.

Figure 2:
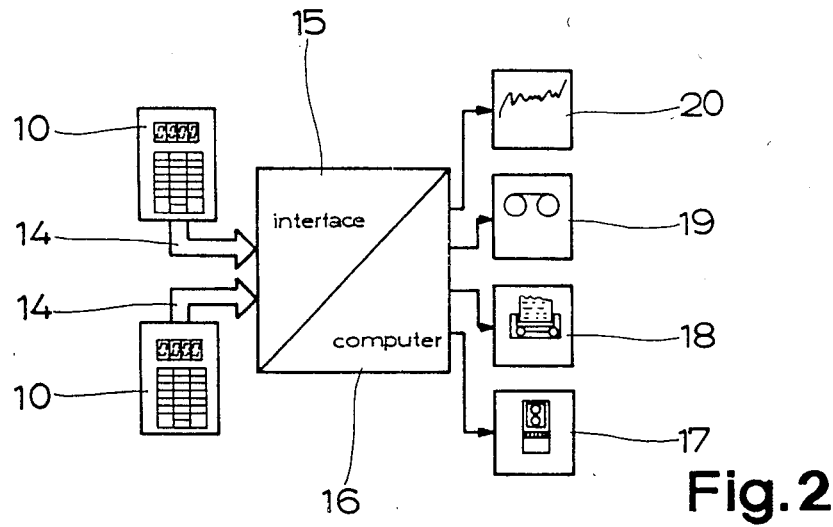
FIG. 2 is a block diagram of an apparatus for indicating and evaluating environmental parameters according to the invention.

As will be apparent from FIG. 2, in a particular mine tunnel or gallery installation, a multiplicity of such devices 10, only two of which have been shown in FIG. 2, can be spaced along the tunnel or gallery and all of these devices may be connected by respective data channels represented at 14 and constituted by the means shown at 13 in FIG. 1 representing the evaluating reporting or display and storage system associated with the device 10. The data channels or interface connections 14 may work into an interface 15 which can also represent a multiplexing, time sharing or other data sampling device feeding the data to the central computer 16.

In the central computer 16, the data collecting from the various storage units 13 of the measuring devices 10 can be evaluated, organized, corrected, normalized and further processed.

The central computer can be connected by a modem 17 or other system to an external computer and may also be provided with various peripherals such as a control terminal 18, a magnetic storage or memory 19 and a user display terminal 20.

Figure 3:
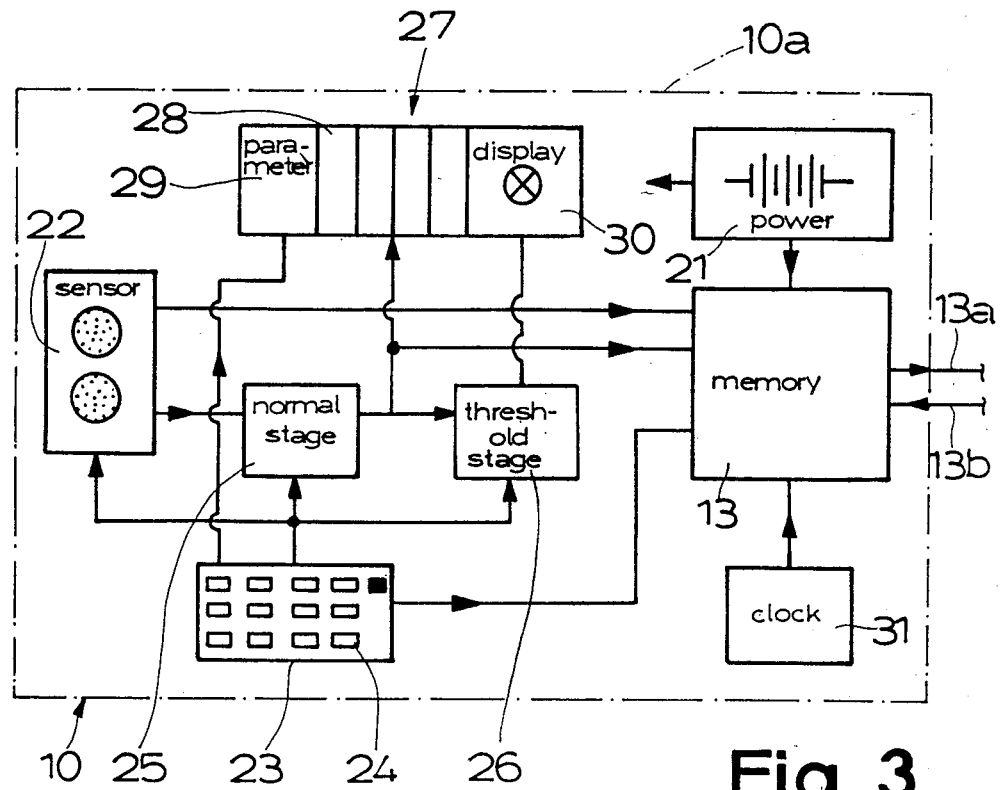
FIG. 3 is a block diagram of an apparatus for use in the system of FIG. 1.

The individual devices 10 can include programmable memories 13 and can have central processing units with respective micro-processors of their own and the central computer 16 can, of course, output control signals to the measuring units to program them and instruct the measuring units as to the data to be stored or released, etc. A block diagram for a measuring device 10 such as has been shown in FIG. 2, is illustrated in FIG. 3 and comprises its own power source 21, e.g. a rechargeable battery. The unit 10 can also comprise a housing represented at 10a including the power source, the parameter sensor and the other electronic circuitry associated therewith, so that it may be moved as a portable unit from place to place in the mine gallery and can be easily carried, connected to data transmission lines or equipped with transmission means, e.g. a radio or other data transmitter.

The device 10 is also equipped with a sensor 22 forming the measuring system which, in a manner not further illustrated in this figure, can include a measuring chamber, a pump for inducing a gas sample into and through this chamber or additional chambers and, of course, an electrical element or transducer respective to one or more parameters of the gas sample, e.g. methane concentrations. The unit 22 can, for example, be a catalytic combustion methane detector.

The operation of such sensors is well known in the art and need not be detailed here. If further data are required, reference may be had to the aforementioned copending application Ser. no. 635,329 and the references mentioned therein.

The measuring device 22 is connected to an actuating unit 23 which can be provided with a number of keys 24 and selecting the operating modes. The unit 22 is also connected with the storage unit 23 which may be equipped with a micro-processor cooperating with the keyboard 22, and the micro-processor forming a controller for all of the circuitry shown in FIG. 3.

The measuring device 22 is also provided with a normalizing stage 25 and the latter can be provided with a threshold stage 26. The actuating unit 23, the measuring stage 25 and the threshold stage 26 are connected with the display 27 which may be an alphanumeric display. The display 27, in particular, may have numeral-displaying windows 28 to display the values of the parameter, a set display window 29 to provide a symbol representing the parameter whose magnitude is displayed and an optical warning device 30 such as a warning lamp.

The circuit is provided with the usual time base or clock 31 for the CPU-memory 13 whose control connection at the various other elements of the circuit have not be illustrated, so that the data in the memory can be stored with an appropriate time base. A connection system for remote transmission of the data is also provided for the circuit and has been represented by the line 13a.

The keyboard 23 permits the measuring device 22 to be switched for selection of the different parameters. This switching can be done automatically and the keyboard 23 may be used only to display the updated data. All of the data collected by the numerous sensors of the measuring device 22 can be stored in the memory 13.

It has been found to be advantageous to provide the keyboard 23 with individual keys 24 which, inter alia, select the parameter to be displayed, input the place or site data utlizing preferably special code number, for setting of the time base for real time, etc. The memory can store the measured values as a function of real time and site.

While FIG. 3 does not illustrate the effect, it will be understood that, when a value derived by the measuring device 22 is an analog measurement, this device can include an analog/digital converter for transforming the measurement into a digital value so that the data can be stored digitally in the memory 13.

With appropriate operation of the selected keys, a character representing the selected data will be displayed in the window 29 followed by the numerical value of the measurement. Should this measurement exceed a threshold level set at 26, e.g. an explosive or toxic limit, the warning lamp 30 will light and the device can also include an acoustic warning for alerting personnel in the vicinity. Furthermore, the system may monitor the parameters which may represent potential danger and should any such parameter exceed the danger threshold, operate the warning device, e.g. the lamp.

The warming lamp 30 can also serve as an indication to the operator that data should be transferred and/or that data values have become inaccurate and the displayed indicia are no longer valid or precise.

Figure 4:
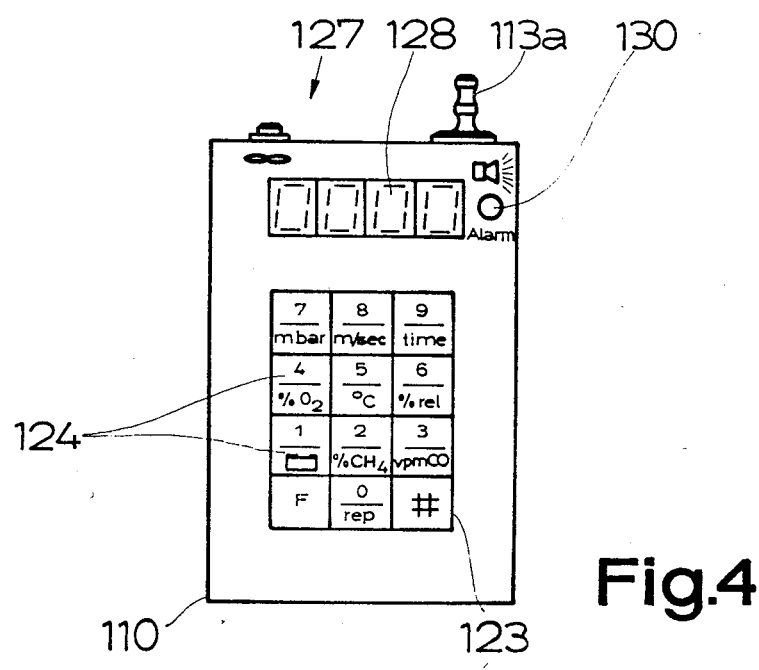
FIG. 4 is an elevational view of the housing of this apparatus.

Not shown in FIG. 3 is that the monitoring unit 13 can have its own energy source so that the memory content can be retained in the event of failure of the power source 21 until the operating power is restored. This prevents loss of the memory contents. FIG. 4 is a front elevational view of a measuring device according to FIG. 1 with a somewhat different configuration of the display terminal represented in FIG. 3 and a somewhat different configuration of the keyboard 123. The device 110 here utilizes a telephone-type keyboard 123 whose keys 124 may be double function keys, capable of numerical input and of selecting the mode and hence the data to be displayed. The F key can shift between the functions. This arrangement also has the numerical display 128 and a warning lamp 130 forming part of the display 127 and a plug 113a can serve to connect the unit to a data bus or to a transmitter. The numerical values of the keys are used for coding the place at which the data is taken into the memory 13 so that the data transmitted from the memory 13 includes the locus of the test.

Figure 5:
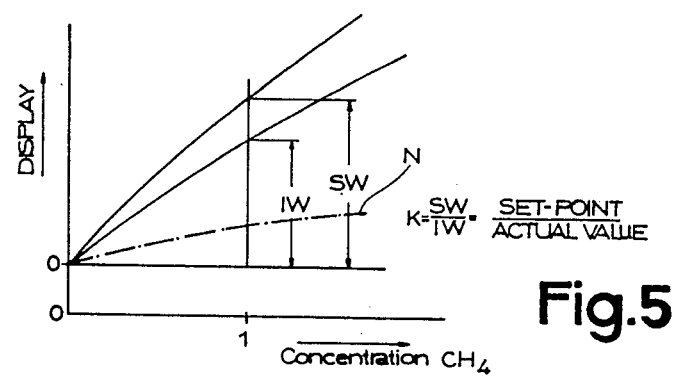
FIG. 5 is a graph illustrating the possible normalization for calibration of the methane concentration parameter.

As has already been noted in connection with FIG. 3, the measuring device 10 has a normalization stage 25 which can be a microprocessor-control micro-electronic component for adjusting the measured value based upon a predetermined standardization or normalization curve. In FIG. 5 I have diagrammed the possible normalization of the measured value of the methane concentration. FIG. 5 represents at N a normalization function, i.e. an amount which must be added to the measured value to yield the desired value corresponding to the measured value in accordance with the sensitivity of the instrument. The correction curve, therefore, is the dot-dash curve N. If the actual measurement is along the lower of the two solid line curves, therefore, desired measurement values will be represented by the upper of these two curves and for a specific value of the concentration, the measured value is represented at IW and the desired value at SW. The normalization function is here empirically determined by actual measurements of standard concentrations of methane, e.g. at zero concentration and at least at one and preferably a plurality of other values along the predicted measurement range.

The normalization function can also be approximated by a polygonal trace as has been illustrated in FIG. 5 in which the measured value M is displayed along the abscissa, the display value is given along the ordinate and the relationship of the two values A and M is determined by a normalization curve which is defined by linear segments in a polygon trace. Over each linear segment, the value is linearized.

Figure 6:
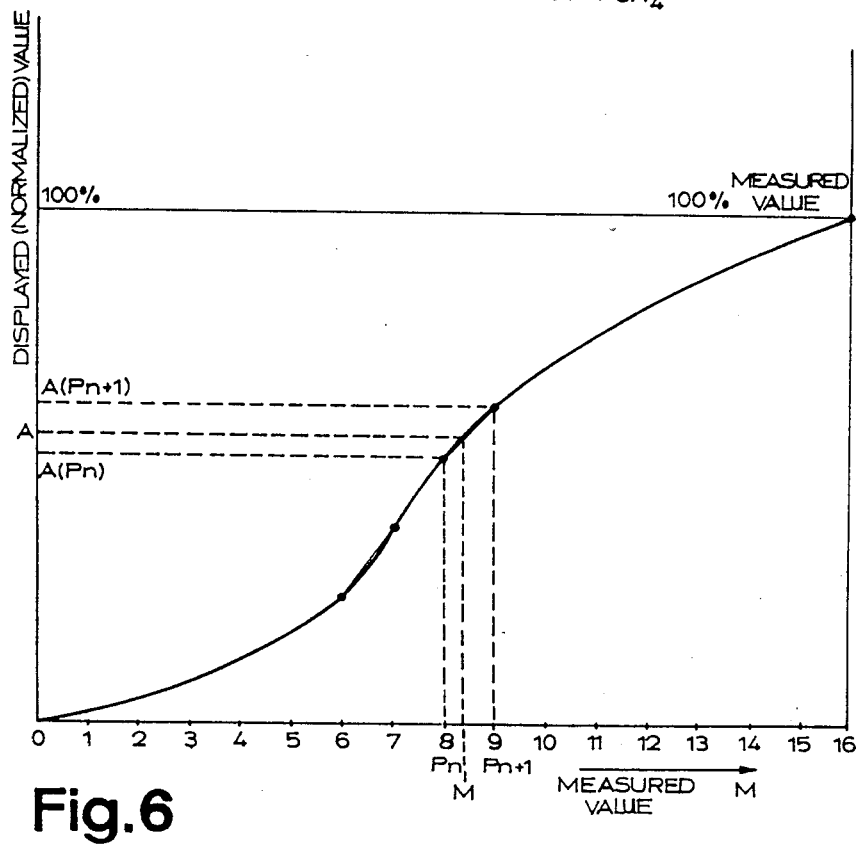
FIG. 6 is a diagram illustrating the possible normalization of another parameter using the device of FIG. 3.

From FIG. 6 is will also be apparent that the width of all of the polygon segments at the abscissa is equal, the width along the abscissa being selected so that the maximum deviation of the polygon segment from the normalization function is of the order of the measurement error of the measuring device. This eliminates poor results due to high measurement errors and also eliminates the need for excessive accuracy in approximation of the normalization curve and thus reduces the memory usage for storage of the normalization curve. Within the normalization stage 25, the normalization function can be calculated based upon the measured values of earlier standard concentrations or parameter settings and this measuring stage thus can have two operating modes, the first for standardization and the development of the normalization curve and the second for use in the manner described.

Figure 7:
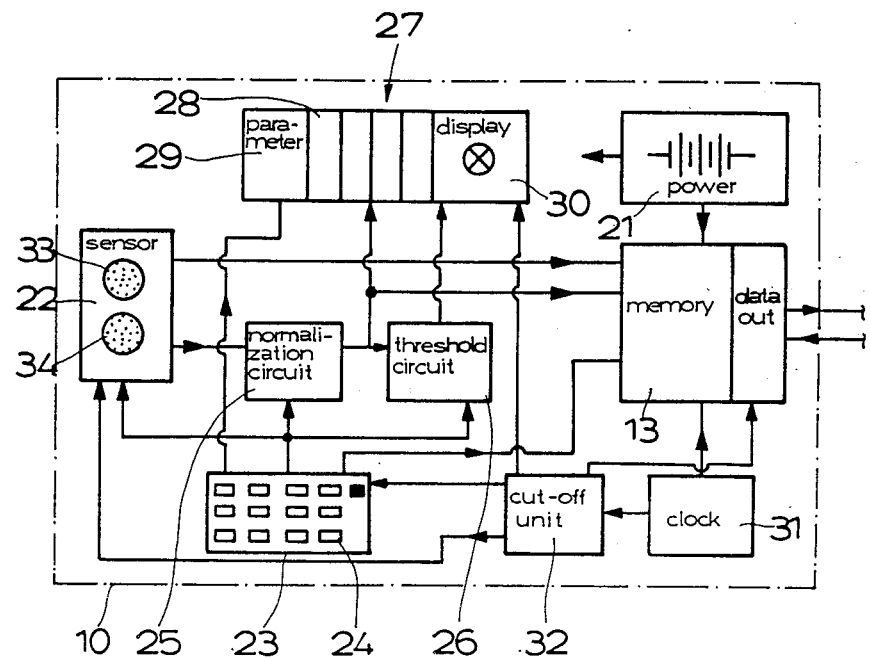
FIG. 7 is a block diagram illustrating another embodiment of the system of FIG. 2.

In FIG. 7 a measuring device 210 has been illustrated which can be used as the device previously described and in which elements corresponding to those of FIG. 3 have identical reference numerals. This device additionally includes a cut-off unit 32. Utilizing the cut-off unit 32, in the event of the development of a dangerous condition such as an excess concentration of methane above the lower explosive limit, I can temporarily cut-off the methane sensor 33 which is operating in a catalytic combustion mode and, in the interim, cut-on a temperature sensor 34 operating in a thermal conductivity mode to maintain a continuous methane concentration measurement.

In other words, upon the development of a danger condition or failure condition, one of the measuring systems can be temporarily cut-off and the other temporarily activated. The same system can be used in accordance with the principles of the copending application Ser. No. 635,329 to turn on periodically a calibration system or as described in the copending application Ser. No. 635,323 to turn on an oxygen sensor and its associated calculator and thus replace the methane detector by a totally safe but equivalent measuring system which also provide a methane concentration output.

The cut-off device 32, when encountering a concentration of methane above the explosive limit such that outputting of information may pose a danger, may also cut-off part of the measuring unit 210 so that the output of the memory 13, the actuating unit 23 and the display 27 are all disabled while the balance of the device, operating in an explosion-proof housing, may remain operative. The measuring device 22 can thus continue to provide an output which is stored and this information can be tapped at a later time.

The measuring device 22 can thus include a first measuring element 33 with high precision and sensitivity but one which may have safety problems or reliability problems, and a second measuring element 34 which can have reduced sensitivity and precision but which is more reliable and does not create safety problems.

When the appropriate condition arises, the cut-off device 32 switches from the more sensitive element to the other element and upon the termination of the danger condition, the system is switched back to the use of the better measuring element. At least upon the termination of the defect condition, the output of the memory 13 is connected to the sampler 14 and the computer automatically by the cut-off unit 32.

In operation, the device can be transported from place to place in the mine gallery and at each location can be plugged into a data transmitting mine. The operator codes the code number of the location into the memory utlizing the keyboard 23 or 123. The various parameters can then be monitored by operation of the keyboard and with each operation the measured parameter is displayed at appropriate normalization. All of the data may be automatically transferred to the memory simultaneously. The data measured can include the air temperature, relative humidity, atmospheric pressure and air speed, for example, and the data displayed include the actual measurements on the normalized or relative measurements based upon the various parameters. These normalized parameters are frequently the more interesting parameters since they are the ones which directly affect personnel in the mines. If the normalized parameters exceed a threshold set in stage 26 for any parameter having an absolute upper limit, the appropriate optical signal 30 will be triggered. While the device does provide immediate information for an operator, it may be desirable simply to leave the device at the site and monitor the data from the central computer via the remote line. Alternatively, the device itself may represent a portion of the data book and upon return to a central station can be plugged into the central computer which can sample the information stored in the memory. In general each device 10 will constitute an electronic weather book for the mine.

Figure 8:
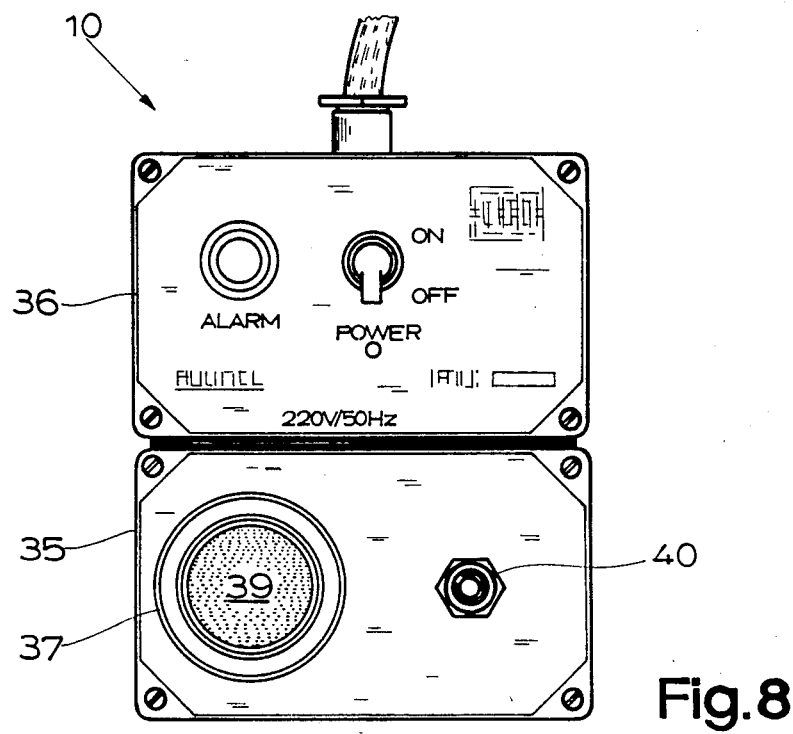
FIG. 8 is an elevational view of the latter apparatus.

In FIG. 8 I have shown another measuring device 310 which is equivalent to the measuring device 10 previously described and also can be used for the measurement and monitoring of gas concentrations in the mine atmosphere. When utilized in a mine the device is calibrated to normalize the methane concentration. The device may also be used as a sniffer for other gases, e.g. in dry-cleaning operations to detect and measure concentrations of perchlor ethylene and trichlorethylene or other dry-cleaning solvents.

Here the measuring unit 35 is connected to an evaluating unit 36. The measuring unit 36 has a diffusion measuring head 37 with a gas sensor 38 which can be an electrically heated metal oxide semiconductor (see FIG. 9). A diffusion-permeable sintered metal plate can form a cap 39 covering the detector 38.

The evaluator 36 includes circuitry of the type described and can include, further, a set point generator to establish the upper value of a concentration, an actual value/set point value comparator whose actual value input derives from the detector 38 and whose set point value from the set point value generator, and an alarm which is connected to the comparator. The measuring unit 35 can have an air inlet 40 connectable to a sniffer probe.

Figure 9:
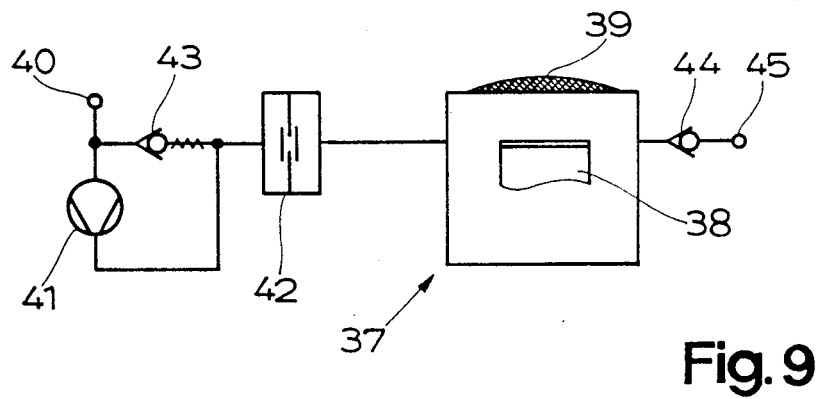
FIG. 9 is a diagram showing the operation of a measuring device for the latter unit.

As can be seen from FIG. 9, the measuring unit 35 may also include a pump 41 which is connected to the second air inlet 40 as already noted and which can be utilized to force gas through the head 37. The pump 41 is here connected via a moisture separator 42 to the diffusion-measuring head 37 which is vented through the check valve 44 to the outlet 45. A bypass valve 43 opens at a predetermined pressure drop across the suction end pressure sides of the pump. The system may operate utilizing the pump to sparge the measuring chamber or, with the modification of the connection, to draw gas to be measured into the chamber.

I claim:

1. A method of measuring and evaluating a parameter of an atmosphere at least at a site at which a dangerous environmental condition can arise which comprises the steps of:
   measuring said parameter to obtain a measured value thereof;
   normalizing said measured value by modifying said measured value in accordance with a predetermined amount corresponding to said measured value to produce a normalized value of said parameter;
   storing at least one of said measured and normalized values; and
   displaying at least one of said normalized and measured values, with said normalized value being displayed at least part of the time, said measured value being normalized in accordance with a corresponding predetermined normalization function, said normalization function being an approximating polygon trace.

2. The method defined in claim 1, further comprising the step of, prior to normalizing said measured value, carrying out a plurality of standard measurements, deriving said normalization function from said standard measurements and thereafter normalizing said measured values.

3. The method defined in claim 2 wherein said standard measurements include a zero point correction measurement.

4. The method defined in claim 2 wherein said standard measurements include at least one intermediate value calibration measurement.

5. The method defined in claim 1 wherein the normalization of said measured value is effected in a parameter-specific manner for said parameter and each of a plurality of additional parameters of said atmosphere which are also measured and normalized.

6. The method defined in claim 5 wherein the measured value of each parameter is respectively linearized.

7. The method defined in claim 5 wherein the measured value of each respective parameter is stored as a function of time.

8. The method defined in claim 5 wherein measurements are taken at a plurality of locations, further comprising the step of storing measured values for each of said parameters for each location in a memory and inputting to said memory a respective code number representing each location associated with particular measured values.

9. The method defined in claim 8 wherein the stored measured values are transferred to a central computer and are evaluated, stored and reported at said central computer.

10. The method defined in claim 1 wherein an expected measurement range for said measured value is subdivided into $2^n$ linear polygon segments forming said polygon trace, n being an integer.

11. The method defined in claim 10 wherein the widths of all of said polygon segments are equal.

12. The method defined in claim 10 wherein the widths of said polygon segments differ from one another.

13. The method defined in claim 10 wherein the measurement of said measured value is effected with a certain measurement error, the number of said polygon segments and the widths thereof being selected in accordance with the magnitude of said measurement error.

14. The method defined in claim 13 wherein the number of widths of the polygon segments are equal for all normalization functions.

15. The method defined in claim 13 wherein the number of widths of the polygon segments also is determined by the shape of the normalization function.

16. The method defined in claim 1 wherein the polygon trace serving as a starting point for said function is determined by at least a plurality of standardized measurements.

17. In a method of measuring and evaluating parameters of an environmental atmosphere, especially the concentrations of various gases in a ventilating stream of a mine, gallery or tunnel, in which a measuring device measures the respective parameter and the measured values of the respective parameters can be remotely transmitted, displayed, processed and stored, and upon the development of a danger condition upon the magnitude of said one of said parameters exceeding a limit, the process is interrupted, the improvement in which the interruption of the process during the occurrence of said dangerous condition is periodically terminated for at least one of the process steps for a period so brief that no danger ensues or the interruption is limited so as not to affect process steps which can continue to be effective without danger, the measurement of one of said parameters being effected with a measuring element of high precision and sensitivity but which poses a danger during said condition and by a second measuring element of reduced precision and sensitivity but which can be safely operated during said condition, further comprising cutting off the operation of said first element while continuing to derive measured values from said second element upon the development of said condition.

18. The improvement defined in claim 17 wherein the periodic termination of the interruption is effected for durations determined by the value of the usual rate of change of the danger-condition-created parameter.

19. The improvement defined in claim 17 wherein remote transmission of data is interrupted during said danger condition and during said danger condition measured values of said parameters continue to be stored in said device.

20. An apparatus for the measurement and evaluation of parameters of a mine atmosphere, comprising:
a housing;
at least one internal power source in said housing;
at least one measuring element on said housing responsive to at least one parameter of said mine atmosphere for generating a measured value thereof;
a memory in said housing for storing said measured value;
a display on said housing for displaying at least a characteristic of said measured value; and
a normalization stage between said element and said display for normalizing said measured value and displaying a normalized value corresponding to said measured value, said stage being constructed and arranged to utilize a polygonal trace as an approximation for a normalization function and can generate said polygonal trace which is thereafter stored in said memory.

21. The apparatus defined in claim 20 wherein said memory is connected with both said element and said normalization stage.

22. The apparatus defined in claim 20 wherein said element is capable of measuring a plurality of such parameters which can be individually stored and displayed.

23. The apparatus defined in claim 22 wherein the measured value of at least one of said parameters is applied to said normalization stage for the normalization of another measured parameter therein.

24. The apparatus defined in claim 22 wherein the normalization stage can be selectively operated with a multiplicity of normalization functions.

25. The apparatus defined in claim 24, further comprising a selector means on said housing operable to select the parameter measured, normalized with a respective normalization function and displayed, said selector means being connected to said normalization stage, said memory and said display.

26. The apparatus defined in claim 25 wherein said display has a standardization/use selected-function display.

27. The apparatus defined in claim 20, further comprising means for enabling standard measurements to generate a normalization function in said stage.

28. The apparatus defined in claim 27, wherein said normalization stage is a first operating mode for receiving standard measurements, a second mode for normalization of a measured value, and is switchable between said modes.

29. The apparatus defined in claim 28, further comprising input means on said housing connected to said stage for inputting standard set point values thereto.

30. The apparatus defined in claim 20, further comprising a clock in said housing connected to said memory for automatically storing measured values of said parameters therein on a time base.

31. The apparatus defined in claim 20, further comprising input means on said housing for coding numbers representing locations at which measurements are made into said memory.

32. The apparatus defined in claim 20, further comprising a threshold stage in said housing receiving one of said values.

33. The apparatus defined in claim 32, further comprising a warning device on said housing connected to said threshold stage.

34. The apparatus defined in claim 33, further comprising means for synchronously switching said threshold stage to said element or said normalization stage.

35. The apparatus defined in claim 20 wherein said display is provided with a symbol display window adapted to display indicia of the parameter measured.

36. The apparatus defined in claim 20, further comprising means for connecting said memory through an interface to a central computer.

37. The apparatus defined in claim 36 wherein said stage is a central computer reprogrammable stage.

38. The apparatus defined in claim 20 wherein said stage is provided with a freely programmable microprocessor.

39. The apparatus defined in claim 20 wherein said element is constructed and arranged to measure a plurality of said parameters.

40. The apparatus defined in claim 39 wherein said stage is constructed and arranged to normalize measured values of a plurality of said parameters using respective polygonal traces stored in said memory and drawn by said stage therefrom.

41. The apparatus defined in claim 40 wherein each of said polygonal traces is stored in said memory at a respective address.

42. The apparatus defined in claim 20 wherein said normalization stage comprises a set point unit for storing a value of a measurement error of said element for a specific measured value, and a difference unit receiving inputs from said set point unit and said element for determining the difference between a value of the normalization function and the corresponding value of the approximating polygonal trace and a comparator for comparing the difference with the value stored in said set point unit.

43. An apparatus for the measurement and evaluation of parameters of a mine atmosphere, comprising:
 a housing;
 at least one internal power source in said housing;
 at least one measuring element on said housing responsive to at least one parameter of said mine atmosphere for generating a measuried value thereof;
 a memory in said housing for storing said measured value;
 a display on said housing for displaying at least a characteristic of said measured value; and
 a cutoff means for cutting off only a limited operational function of the apparatus upon the development of a danger condition in the form of an increase in the magnitude of one of said parameters beyond a predetermined level, said element having a first measuring sensor with high precision and high sensitivity and a second measuring element with lower precision and sensitivity, said cutoff means terminating the operation of said first sensor and activating said second sensor upon the development of said condition.

44. The apparatus defined in claim 43 wherein said cutoff means periodically restores brief operation of the apparatus, portions which have been cut off during said condition and following termination of said condition restores continuous operation thereof.

45. The apparatus defined in claim 43 wherein said cutoff means only cuts off the output of said memory, cuts off said element and cuts off said display.

46. The apparatus defined in claim 43 wherein said memory is connected so that it continues to receive measured values and only upon termination of said condition can display and transfer stored values.

47. In a mesuring device for measuring and monitoring the concentration of a gas in an atmosphere which comprises a measuring unit and an evaluating unit connected to said measuring unit, said measuring unit having a diffusion head and a gas concentration indicator covered by a diffusion cap, the evaluating unit comprising a set point generator, an actual value/set point value comparator and an alarm connected to said comparator, said measuring unit having an air inlet, the improvement wherein said measuring unit includes a pump having a suction side connected to said inlet and a pressure side connected to said head and wherein parallel to said pump a bypass valve is provided between the pressure and intake sides thereof and is opened upon the development of a predetermined pressure drop across the pump.

48. The improvement defined in claim 47 wherein said pump is connected to the diffusion measuring head at a location behind the diffusion protective cap of said diffusion measuring head.

49. The improvement defined in claim 48 wherein a moisture separator is provided between said pump and said diffusion measuring head.

50. The improvement defined in claim 47 wherein said measuring unit includes a discharge outlet opening to the atmosphere and connected to said head by a check valve.

* * * * *